United States Patent

Walker et al.

[11] Patent Number: 5,856,553
[45] Date of Patent: Jan. 5, 1999

[54] CARBONIC ACID 3-METHOXYCARBONYLOXY-2,2,4,4-TETRAMETHYL-CYCLOBUTYL ESTER METHYL ESTER AND METHOD OF MAKING THEREFOR

[75] Inventors: Theodore R. Walker; Jean C. Fleischer, both of Kingsport, Tenn.; William R. Darnell, Weber City, Va.

[73] Assignee: Eastman Chemical Company, Kingsport, Tenn.

[21] Appl. No.: 996,454

[22] Filed: Dec. 23, 1997

Related U.S. Application Data

[60] Provisional application No. 60/034,989, Dec. 28, 1996.
[51] Int. Cl.$^6$ ..................................................... C07C 69/96
[52] U.S. Cl. ............................................. 558/265; 558/277
[58] Field of Search ...................................... 558/265, 277

[56] References Cited

U.S. PATENT DOCUMENTS

| | | |
|---|---|---|
| 2,210,817 | 8/1940 | Peterson . |
| 2,787,632 | 4/1957 | Stevens . |
| 2,789,968 | 4/1957 | Reynolds et al. . |
| 3,022,272 | 2/1962 | Schnell et al. . |
| 3,030,335 | 4/1962 | Goldberg . |
| 3,313,777 | 4/1967 | Elam et al. . |
| 3,317,466 | 5/1967 | Caldwell et al. . |
| 3,335,111 | 8/1967 | Pray et al. . |
| 3,772,405 | 11/1973 | Hamb . |
| 4,182,726 | 1/1980 | Illuminati et al. . |
| 4,263,364 | 4/1981 | Seymour et al. . |
| 4,350,805 | 9/1982 | Jackson, Jr. et al. . |
| 4,585,854 | 4/1986 | Tung et al. . |
| 5,171,830 | 12/1992 | Grey . |

FOREIGN PATENT DOCUMENTS

| | | |
|---|---|---|
| 63-92644 | 4/1988 | Japan . |
| 64-1724 | 1/1989 | Japan . |

OTHER PUBLICATIONS

Caldwell et al., Defensive Publication T858,012, 858 O.G. 43, Jan. 7, 1969.

Gilkey et al., Denfense Publication T873,016, 873 O.G. 1033, Apr. 28, 1970.

Coover et al., Defensive Publication T875,010, 875 O.G. 342, Jun. 9, 1970.

Haggin, "Catalytic Cosynthesis Method Developed," Chemical and Engineering News, pp. 25–26, May 4, 1992.

Gawlak et al., "Polycarbonates from the 2,2,4,4,–Tetramethylcyclobutane–1,3–Diols," Chemistry And Industry, pp. 1148–1149, Jun. 23, 1962.

Schnell "Chemistry And Physics of Polycarbonates, Polymer Reviews," vol. 9, Interscience Publishers (Germany), pp. 9–24, 1964.

*Primary Examiner*—Johann Richter
*Assistant Examiner*—Joseph Murray
*Attorney, Agent, or Firm*—B. J. Boshears; Harry J. Gwinnell

[57] ABSTRACT

The invention relates to the compounds having the structures I and II:

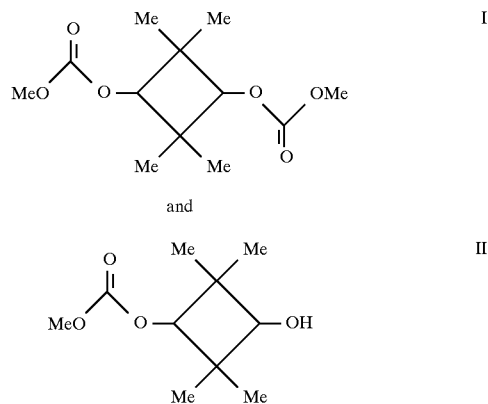

The invention also relates to a method of making the compound having the structure I by mixing 2,2,4,4-tetramethyl-1,3-cyclobutanediol; dimethyl carbonate; and a basic catalyst, and heating the mixture.

24 Claims, No Drawings

CARBONIC ACID 3-METHOXYCARBONYLOXY-2,2,4,4-TETRAMETHYL-CYCLOBUTYL ESTER METHYL ESTER AND METHOD OF MAKING THEREFOR

CROSS REFERENCE TO RELATED APPLICATIONS

This application claims priority upon United States provisional application Ser. No. 60/034,989, filed Dec. 28, 1996, and the contents of which are herein incorporated by this reference in their entirety.

FIELD OF THE INVENTION

The present invention relates to a new compound, carbonic acid 3-methoxycarbonyloxy-2,2,4,4-tetramethyl-cyclobutyl ester methyl ester, and a method of making therefor.

BACKGROUND

Poly(2,2,4,4-tetramethyl-1,3-cyclobutylene carbonate) is a useful polymer for making molded articles. However, the art does not disclose an efficient method for the preparation of high molecular weight poly(2,2,4,4-tetratmethyl-1,3-cyclobutylene carbonate).

Defensive Publication T858,012 discloses a melt method of preparing poly(2,2,4,4-tetramethyl-1,3cyclobutylene carbonate) by reacting 2,2,4,4-tetramethyl-1,3-cyclobutanediol, hereinafter referred to as "TMCD" for convenience, with the bis(ethyl carbonate) of TMCD in the presence of a dibutyltin oxide catalyst. However, this process only produces low molecular weight and discolored polymers having inherent viscosities below 0.4 dL/g.

Bis(phenyl carbonates) such as those used in U.S. Pat. No. 3,335,111 are known in the art as monomers for the production of polycarbonates. However, these aromatic monomers are expensive to produce and the phenol by-product ultimately imparts some undesirable color to the polymer.

In light of the above, it would be desirable to have a bis alkyl carbonate of TMCD and a method of making therefor that can be used in the production of high molecular weight poly(2,2,4,4-tetramethyl-1,3-cyclobutylene carbonate).

SUMMARY OF THE INVENTION

In accordance with the purpose(s) of this invention, as embodied and broadly described herein, this invention, in one aspect, relates to a compound having the structure I:

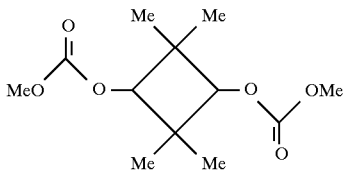

The invention further relates to a compound having the structure II:

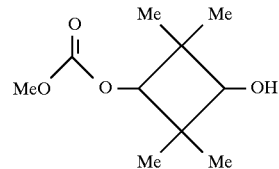

The invention further relates to a method for making a compound having the structure I:

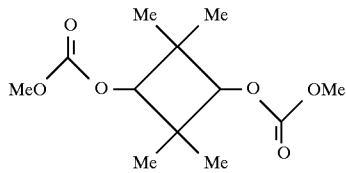

comprising,
(a) admixing
(i) 2,2,4,4-tetramethyl-1,3-cyclobutanediol;
(ii) dimethyl carbonate; and
(iii) a basic catalyst, and
(b) heating the admixture of step (a).

The invention further relates to a process comprising reacting 2,2,4,4-tetramethyl-1,3-cyclobutanediol and dimethyl carbonate in the presence of a basic catalyst at a pressure and temperature sufficient to form carbonic acid 3-methoxycarbonyloxy-2,2,4,4-tetramethyl-cyclobutyl ester methyl ester.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of preferred embodiments of the invention and the Examples included therein.

Before the present compositions of matter and methods are disclosed and described, it is to be understood that this invention is not limited to specific synthetic methods or to particular formulations, as such may, of course, vary. It is also to be understood that the terminology used herein is for the purpose of describing particular embodiments only and is not intended to be limiting.

In this specification and in the claims which follow, reference will be made to a number of terms which shall be defined to have the following meanings:

The singular forms "a," "an" and "the" include plural referents unless the context clearly dictates otherwise.

"Optional" or "optionally" means that the subsequently described event or circumstance may or may not occur, and that the description includes instances where said event or circumstance occurs and instances where it does not.

In accordance with the purpose(s) of this invention, as embodied and broadly described herein, this invention, in one aspect, relates to a compound having the structure I:

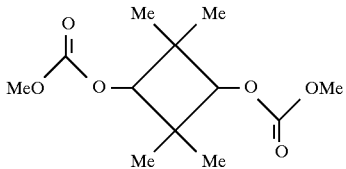

The invention further relates to a compound having the structure II:

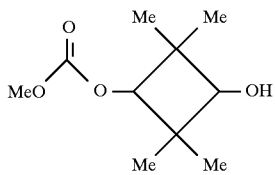

The invention fiber relates to a method for making a compound having the structure I:

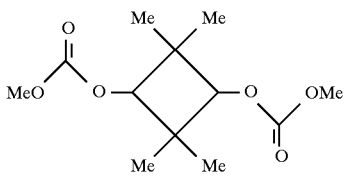

comprising,
 (a) admixing
  (i) 2,2,4,4-tetramethyl-1,3-cyclobutanediol;
  (ii) dimethyl carbonate; and
  (iii) a basic catalyst, and
 (b) heating the admixture of step (a).

The applicants have unexpectedly discovered a new compound and method of making therefor. Carbonic acid 3-methoxycarbonyloxy-2,2,4,4-tetramethylcyclobutyl ester methyl ester, herein referred to as "TMCD bis(methyl carbonate)" for convenience, is not disclosed in the art.

The applicants unexpectedly discovered that TMCD bis (methyl carbonate) is useful in the production of high molecular weight poly(2,2,4,4-tetramethyl-1,3-cyclobutylene carbonate). This discovery was particularly surprising since there has been no motivation or direction in the art to use TMCD bis(methyl carbonate) for the production of poly(2,2,4,4-tetramethyl-1,3-cyclobutylene carbonate), even though the corresponding bis(ethyl carbonate) analog has been disclosed and used in the production of poly(2,2,4,4-tetramethyl-1,3-cyclobutylene carbonate).

One advantage of the present invention is that the purity of the resultant TMCD bis(methyl carbonate) produced by the present invention is very high. It is known in the art that ether formation is usually a problem when an alcohol reacts with dimethyl carbonate. In fact, when the bis(methyl carbonate) of bisphenol A is made from dimethyl carbonate, it is contaminated with the methyl ether of bisphenol A, rendering it useless as a monomer.

In light of the above, there was not motivation or direction to make TMCD bis(methyl carbonate) from TMCD and dimethyl carbonate because even small amounts of the methyl ether of TMCD can act as a terminator and render TMCD bis(methyl carbonate) useless as a polycarbonate monomer. The applicants have discovered that the methyl ether of TMCD is not formed in the present invention.

U.S. Pat. No. 4,350,805 discloses a process of making the bis(methyl carbonate) of bisphenol A by the reacting bisphenol A with methyl chloroformate. The applicants have determined that this method produces TMCD bis(methyl carbonate), wherein the hydroxyl content is greater than 20 mole %. In the present invention, TMCD bis(methyl carbonate) has less than 2 mole % unreacted hydroxyl groups.

Another advantage of the present invention is that the reaction of dimethyl carbonate and the highly sterically hindered TMCD goes to completion much more rapidly than prior art processes. Producing TMCD bis(methyl carbonate) by the present invention is, therefore, a very economical and effective way of producing TMCD bis(methyl carbonate) that can be used for the polymerization of high molecular weight poly(2,2,4,4-tetramethyl-1,3-cyclobutylene carbonate).

In one embodiment, a mixture of TMCD and dimethyl carbonate are admixed in the presence of a basic catalyst at a pressure and temperature sufficient to form TMCD bis (methyl carbonate).

In one embodiment, TMCD can be the cis isomer, the trans, isomer, or a mixture thereof. In another embodiment, the concentration of TMCD is preferably about 5 to 40 mole %, preferably from about 10 to 20 mole %, and more preferably 15 mole %. If more than 40 mole % TMCD is used, more polycarbonate oligomer will be produced, which results in the formation a low viscosity polymer. When less than about 5 mole % of TMCD is used, the reaction is slow and may higher concentration of basic catalyst.

Any catalyst that generates the glycol oxide anion is suitable for use in the process of the present invention. Examples of basic catalysts include, but are not limited to, oxides, hydrides and hydroxides of alkali metals; free alkali metals; butyl lithium; phenyl lithium; sodium aluminate; alkali metal alkoxides such as sodium methoxide; and amines such as triethylamine and 4-(dimethylamino) pyridine. In a preferred embodiment, the basic catalyst is lithium, sodium, an alkali metal alkoxide, or a combination thereof.

In one embodiment, the catalyst concentration is from about 0.015 to 0.7 mole %, preferably from about 0.03 to 0.1 mole %. Catalyst concentration may vary depending upon the solubility of the catalyst. With some catalysts, a reaction time of 30 to 90 minutes was observed, which may be due to poor solubility of the catalyst. In one embodiment, if the basic catalyst is dissolved in a solvent, preferably methanol, prior to admixing with TMCD, the reaction occurs immediately.

In another embodiment, the heating step is from 90° to 100° C., which is the reflux temperature of dimethyl carbonate. An azeotrope of methanol and dimethyl carbonate is formed as the by-product of the interchange reaction. In one embodiment, the azeotrope can be slowly removed from the reaction mixture upon reflux in order for the reaction to go to completion. In another embodiment, the reaction volume lost through distillation can be replaced by periodic addition of dimethyl carbonate to the reaction mixture.

The heating step is continued until a suitable amount of hydroxyl groups have reacted with dimethyl carbonate to produce TMCD bis(methyl carbonate). After the azeotrope has been substantially formed and removed from the mixture, the reaction can be continued until only a trace amount of a compound having the structure II, herein referred to as TMCD mono(methyl carbonate), is present.

TMCD mono(methyl carbonate) is not disclosed in the art. In one embodiment, TMCD bis(methyl carbonate) contains less than or equal to 10 mole % unreacted hydroxyl groups, preferably less than 2 mole % unreacted hydroxyl groups.

In one embodiment, TMCD bis(methyl carbonate) can be purified by vacuum distillation or recrystallization. Recrystallization tends to alter the cis|trans ratio due to differing solubilities of the isomers. In another embodiment, if TMCD bis(methyl carbonate) is purified by distillation, the basic catalyst is deactivated or removed before distillation. If the basic catalyst is not removed or deactivated, TMCD bis (methyl carbonate) will oligomerize during distillation and, susequently, low polymer yields.

In one embodiment, the catalyst can be deactivated by contacting TMCD bis(methyl carbonate) with a non-volatile carboxylic acid. Volatile acids such as acetic acid will neutralize the catalyst initially, but under conditions of vacuum distillation, the neutralization reaction is reversed so that acetic acid distills out, thus regenerating catalyst. Examples of carboxylic acids useful for deactivating the basic catalyst include, but are not limited to, 1,4-cyclohexanedicarboxylic acid or sebacic acid.

In another embodiment, the catalyst can be removed prior to distillation purification. In one embodiment, the basic catalyst is removed by extracting TMCD bis(methyl carbonate) with a dilute acid.

TMCD bis(methyl carbonate) can be qualitatively and quantitatively determined by gas chromatography (GC) and by thin layer chromatography (TLC), which are demonstrated in the forthcoming Examples.

TMCD bis(methyl carbonate) has been found to be exceptionally useful in the production of poly(2,2,4,4-tetramethyl-1,3-cyclobutylene carbonate) by a process disclosed in applicants' provisional application (Ser. No. 60/034,992), herein incorporated herein in its entirety. Described therein is a melt process of preparing poly(2,2,4,4-tetramethyl-,3-cyclobutylene carbonate) comprising condensing TMCD bis(methyl carbonate) in the presence of a basic catalyst.

EXAMPLES

The following examples are put forth so as to provide those of ordinary skill in the art with a complete disclosure and description of how the compositions of matter and methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature and pressure is at or near atmospheric.

Thin Layer Chromatography (TLC) Procedure

5 L of concentrated sulfuric acid was added slowly to a mixture of 5 mL of p-anisaldehyde in 90 mL of absolute ethanol. After mixing thoroughly, 2 mL acetic acid was added. A TLC plate was spotted with the reaction mixture and developed with 5% methanol in methylene chloride. To visualize the separate spots, the plate was sprayed with or dipped into the anisaldehyde solution. Excess was removed with a tissue. Blue-violet spots were produced when the plate was subsequently heated on a hot plate. A mixture containing TMCD bis(methyl carbonate), TMCD monocarbonate, and TMCD showed TMCD bis(methyl carbonate) as the upper spot, TMCD monocarbonate as the middle spot, and TMCD as the lower spot.

Example 1

The following example illustrates the preparation of 2,2,4,4-tetramethyl-1,3-cyclobutanediyl bis(methyl carbonate) by the process of the present invention using a molar ratio of dimethyl carbonate to TMCD of about 7:1.

1890 mL of dimethyl carbonate, 432 grams of TMCD, and 6.23 grams of solid lithium isoproxide were added to a 5 L flask equipped with stirrer, dropping funnel, and 15-inch Vigreux column. The mixture was refluxed with stirring and the methanol/dimethyl carbonate azeotrope was removed slowly at a rate of about 3 mL per minute. The azeotrope was collected in a graduated receiver, and the volume removed was replaced by periodic addition of dimethyl carbonate through the dropping funnel. Reaction was continued until the head temperature was greater than 85° C. The reaction was followed by thin layer chromatography until only a trace amount of TMCD monocarbonate remained.

The reaction mixture was filtered warm to remove a small amount of solids. The catalyst was deactivated by adding 8.6 grams trans-1,4-cyclohexanedicarboxylic acid and stirring at from 40° to 45° C. for about 1 hour. The mixture was filtered to remove a small amount of solids, and the filtrate was stripped of low boilers in a rotary evaporator under reduced pressure. The remaining mixture was transferred to a distillation flask and vacuum distilled through a 15-inch column packed with glass rings to give a first cut of 97 grams and a second cut of 462 grams.

The first cut was 2,2,4,4-tetramethyl-1,3cyclobutanediyl bis(methyl carbonate) containing 3 to 4 mole % mono (methyl carbonate), as determined by GC. The second cut was 2,2,4,4-tetramethyl-1,3-cyclobutanediyl bis(methyl carbonate) containing 1 to 2 mole % mono(methyl carbonate). The combined yield was 72%.

Example 2

The procedure of Example 1 was followed except that the molar ratio of dimethyl carbonate to TMCD was increased from 7:1 to 14:1. The first cut was TMCD bis(methyl carbonate) containing 1 to 2 mole % TMCD monocarbonate and the second cut is TMCD bis(methyl carbonate) containing less than 1 mole % TMCD monocarbonate. The combined yield was 85%.

This Example shows that an increase in dimethyl carbonate molar ratio from 7:1 to 14:1 causes a 10% improvement in yield and a 1 to 2 mole % decrease in the presence of mono(methyl carbonates).

Example 3

The procedure of Example 1 was followed except that the catalyst was not deactivated with 1,4-cyclohexanedicarboxylic acid. Instead, the catalyst was extracted with dilute HCl. Afterwards the reaction mixture was dried over sodium sulfate and distilled.

The first cut of 20 grams (2.5% of theoretical yield) was discarded. The second cut was TMCD bis(methyl carbonate) containing 1 to 2 mole % TMCD mono(methyl carbonate). The yield was 58%.

Example 4

The procedure of Example 1 was followed except that the catalyst was a solution of 1.62 grams sodium methoxide in 40-mL methanol instead of 6.2 grams of solid lithium isoproxide. The first cut contained 3 to 4 mole % mono (methyl carbonate) and the second cut contained 1 to 2 mole % TMCD mono(methyl carbonate). The combined yield was 69%.

Example 5

The procedure of Example 4 was followed except that the catalyst level was reduced to 0.40 grams (25% as much as in Example 4). The first cut contained 3 to 4 mole % mono(methyl carbonate) and the second cut contained 1 to 2 mole % mono(methyl carbonate). The combined yield was 63%.

Example 6

The procedure of Example 1 was followed except that the catalyst was 2.0 grams of sodium metal spheres instead of 6.2 grams of lithium isoproxide. The first cut contained 2 to 3 mole % mono(methyl carbonate) and the second cut contained less than 2 mole % mono(methyl carbonate). The combined yield was 72%.

Example 7

This Example illustrates the method of isolating TMCD bis(methyl carbonate) by crystallization rather than distillation. This Example also illustrates the process of the present invention using higher concentrations of TMCD than the previous Examples.

Using TMCD containing about 50 mole % trans isomer, the procedure of Example 6 was followed with a 4:1 molar ratio of dimethyl carbonate to TMCD until TLC revealed only a trace of mono(methyl carbonate). The mixture was filtered warm to remove a small amount of solids. The catalyst was not deactivated. Low boilers were removed from the filtrate in a rotary evaporator, and the residue was slurried in about 900 mL of petroleum ether. Filtration gave TMCD bis(methyl carbonate) in 37% yield as a colorless solid, which GC showed to be high purity bis(methyl carbonate) containing 96% trans isomer. Removal of solvent from the filtrate gave TMCD bis(methyl carbonate) in 48% yield and 99% purity (by GC). The trans content was 30 mole %.

Example 8

In this Example, the procedure of Example 1 was followed except that the catalyst used was 22 mL tributylamine. The first distillation cut was TMCD bis(methyl carbonate) in 16.5% yield containing about 8 mole % mono(methyl carbonate). The second cut was in 57% yield containing 1.8 mole % mono(methyl carbonate).

Example 9

In this Example, the procedure of Example 1 was followed except that the catalyst was 11 grams of 4-(dimethylamino)-pyridine. The first distillation cut was TMCD bis(methyl carbonate) in 11.5% yield containing about 9 mole % mono(methyl carbonate). The second cut was TMCD bis(methyl carbonate) in 58% yield containing less than I mole % mono(methyl carbonate).

Example 10

This Example shows that methyl chloroformate reacts poorly with TMCD, giving only about 50% conversion of TMCD to TMCD bis(methyl carbonate). The same procedure gives TMCD bis(methyl carbonate) of 2,2-dimethyl-1,3-propanediol in 93% yield.

A mixture of 216 grams TMCD and 750-mL pyridine was cooled at 10° to 20° C. 500 grams methyl chloroformate was added dropwise. When the addition was complete, the ice in the bath was allowed to melt and the mixture was stirred overnight at ambient temperature. The reaction mixture was poured into about 3 liters of warm water. The oily product (bottom layer) was separated. The aqueous lay was extracted with 450 mL toluene. The combined oily product and toluene layer was washed with water, washed twice with 450 mL portions of 10% hydrochloric acid, and again with water. The toluene solution was dried over magnesium sulfate and the toluene was removed in a rotary evaporator to give 342.7 grams product. NMR (nuclear magnetic resonance spectroscopy) analysis showed the product to contain 51 mole % TMCD bis(methyl carbonate) and 49 mole % mono(methyl carbonate).

When the above procedure was repeated with heptane replacing toluene in the work-up, 322.5 grams of product was obtained that contained 68 mole % bis(methyl carbonate) and 32 mole % mono(methyl carbonate).

Example 11

Table 1 illustrates the suitable reaction tines required for carrying out the process of the present invention. Suitable reaction time is determined by the reaction of hydroxyl groups, as shown by the disappearance of TMCD monocarbonate. Table 1 illustrates how the reaction is dependent upon the concentration of catalyst.

TABLE 1

| Reaction Time as Measured by Disappearance of TMCD Monocarbonate | | | | | |
|---|---|---|---|---|---|
| | | TMCD Monocarbonate, wt.% | | | |
| Catalyst | ppm Cat. | 45 min | 90 min | 120 min | 150 min |
| Na | 50 | 33.6 | 29 | 0.6 | 150 min |
| Na | 100 | 5.2 | 0.5 | 0.2 | 0 |
| Li isopropoxide | 50 | 27.3 | 2.5 | 0.6 | 0 |
| Li isopropoxide | 100 | 9.7 | 0.3 | 0.1 | 0 |

*ppm Catalyst is based on weight of TMCD. Lithium isopropoxide was calculated as ppm lithium.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed:

1. A compound having the structure I:

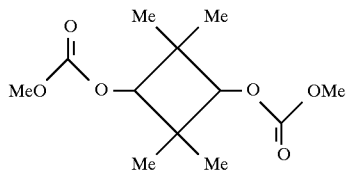

2. A compound having the structure II:

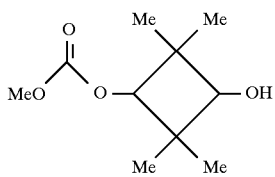

3. A method for making a compound having the structure I:

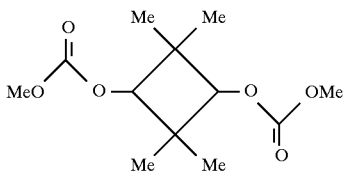

comprising,
(a) admixing
(i) 2,2,4,4-tetramethyl-1,3-cyclobutanediol;
(ii) dimethyl carbonate; and
(iii) a basic catalyst, and
(b) heating the admixture of step (a).

4. The method of claim 3, wherein the 2,2,4,4-tetramethyl-1,3-cyclobutanediol is from 5 to 40 mole %, wherein the sum of components (i)-(iii) is 100 mole %.

5. The method of claim 3, wherein the 2,2,4,4-tetramethyl-1,3-cyclobutanediol is from 10 to 20 mole %, wherein the sum of components (i)-(iii) is 100 mole %.

6. The method of claim 3, wherein the basic catalyst comprises an alkali metal oxide, and alkali metal hydride, an alkali metal hydroxide, an alkali metal, an alkali metal alkoxide, butyllithium, phenyl lithium, sodium aluminate, an amine, or a combination thereof.

7. The method of claim 6, wherein the alkali metal alkoxide comprises sodium methoxide.

8. The method of claim 6, wherein the amine comprises triethylamine, 4-dimethylaminopyridine, or a combination thereof.

9. The method of claim 3, wherein the basic catalyst is lithium, sodium, a sodium alkoxide, a lithium alkoxide, or a combination thereof.

10. The method of claim 3, wherein the basic catalyst is from 0.015 to 0.7 mole %, wherein the sum of components (i)-(iii) is equal to 100 mole %.

11. The method of claim 3, wherein the basic catalyst is from 0.03 to 0.1 mole %, wherein the sum of components (i)-(iii) is equal to 100 mole %.

12. The method of claim 3, further comprising, prior to step (a), admixing the basic catalyst with a solvent.

13. The method of claim 12, wherein the solvent is methanol.

14. The method of claim 3, wherein the heating step is from 90° to 100° C.

15. The method of claim 3, wherein the heating step is the reflux temperature of dimethyl carbonate.

16. The method of claim 3, further comprising, during the heating step, removing dimethyl carbonate by distillation.

17. The method of claim 3, wherein the heating step is of a sufficient time to produce a mixture of the compound having the structure I and II:

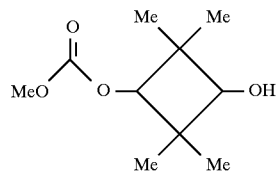

wherein, the mixture has less than or equal to 10 mole % of the compound having the structure II.

18. The method of claim 17, wherein the amount of the compound having the structure II is less than or equal to 2 mole %.

19. The method of claim 3, further comprising, after step (b), purifing the compound having the structure I.

20. The method of claim 19, wherein the purifyng step comprises recrystallizing or vacuum distilling the compound having the structure I.

21. The method of claim 19, wherein the purifying step comprises distilling the compound having the structure I, wherein prior to the distilling step, deactivating the basic catalyst.

22. The method of claim 21, wherein the deactivating step comprises contacting the admixture comprising the compound having the structure I produced after the heating step (b) with an acid.

23. The method of claim 22, wherein the acid comprises a carboxylic acid.

24. The method of claim 23, wherein the carboxylic acid comprises 1,4-cyclohexanedicarboxylic acid, sebacic acid, or a combination thereof.

* * * * *